United States Patent [19]

Katayama et al.

[11] 4,136,079
[45] Jan. 23, 1979

[54] UREA COMPOUND HAVING CARBOXYLATE RADICAL AND METHOD FOR PRODUCING THE SAME

[75] Inventors: Shitomi Katayama; Nobuaki Koyama; Hajime Shimabukuro, all of Yokohama; Kiyoshi Jin, Shiki, all of Japan

[73] Assignee: NHK Spring Co., Ltd., Yokohama, Japan

[21] Appl. No.: 878,911

[22] Filed: Feb. 17, 1978

[30] Foreign Application Priority Data

Feb. 25, 1977 [JP] Japan .................................. 52-19981

[51] Int. Cl.$^2$ .............................................. C08G 18/32
[52] U.S. Cl. .................... 260/37 N; 260/40 R; 260/75 TN; 260/77.5 CH; 528/61; 528/71
[58] Field of Search .................. 260/77.5 CH, 75 TN, 260/37 N, 40 R

[56] References Cited

U.S. PATENT DOCUMENTS

| 3,851,761 | 12/1974 | Martin et al. ................ 260/77.5 CH |
| 3,870,684 | 3/1975 | Witt et al. .................... 260/77.5 CH |

*Primary Examiner*—M. J. Welsh

[57] ABSTRACT

A urea compound having carboxylate radical is obtained by reaction of aminoaminocarboxylate represented by the formula:

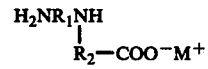

(where $R_1$ *1* is a hydrocarbon-based radical, and $R_2$ is ethylene radical or a substituted ethylene radical) with diisocyanate, optionally in the presence of diamine and/or water. The reaction may be achieved by interfacial polymerization, solution polymerization, or solvent-free polymerization.

50 Claims, No Drawings

UREA COMPOUND HAVING CARBOXYLATE RADICAL AND METHOD FOR PRODUCING THE SAME

BACKGROUND OF THE INVENTION

I. Field of the Invention

This invention relates to a new electrolyte compound and a method for preparing the same, and more specifically to a urea compound having carboxylate radical and a method for preparing the same. (The "urea compound having carboxylate radical" may herein be alternatively referred to as "carboxylate urea compound" or "carboxylate polyurea.")

II. Description of the Prior Art

Many synthetic high molecular weight substances are defective in moisture-absorptive property, antistatic property, dyeability, etc., so that there have conventionally been used additives such as plasticizers or surface active agents to be mixed in these substances for the improvement of such properties thereof. These ways of improvement have, however, been accompanied by several shortcomings, such as the additive's degradation with time, phase separation, etc. Therefore, it is most preferred to independently polymerize or copolymerize moisture- or water-absorptive monomers. However, in carrying out polyaddition or polycondensation, a fully attention should be paid to the selections of raw materials and polymerization method, because a moisture- or water-absorptive functional group contained in some kind of the raw materials may give rise to the inhibition or prohibition of polymerization due to the effect of polarity of the functional group, or may be consumed and dissipated during the polymerization reaction.

SUMMARY OF THE INVENTION

An object of this invention is to provide a carboxylate urea compound having many advantages over the conventional high molecular weight substances with respect to such properties as water-solubility, hydrophilic property, water-absorptive property, and antistatic property, and to provide a method for producing the same.

The urea compound having carboxylate radical of the invention may generally be represented by the general formula:

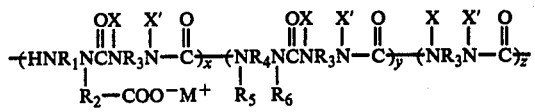

where $R_1$ is a divalent hydrocarbon-based radical having 2 to 17 carbon atoms or a divalent polymer radical having an average molecular weight of 10,000 or less; $R_2$ is

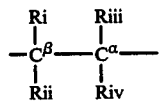

radical, Ri, Rii, Riii and Riv are each independently hydrogen atom, a monovalent hydrocarbon-based radical having 1 to 10 carbon atoms or any other monovalent radical unreactive with isocyanato or amino radicals, at least one of Ri and Rii being hydrogen atom; $R_3$ is a divalent hydrocarbon-based radical having 4 to 25 carbon atoms or a polyether or polyester radical having an average molecular weight of 10,000 or less; $R_4$ is a divalent hydrocarbon-based radical having 2 to 17 carbon atoms; $R_5$ and $R_6$ are each independently hydrogen atom or a monovalent hydrocarbon-based radical having 1 to 8 carbon atoms, or $R_5$ and $R_6$ are divalent hydrocarbon-based radicals forming together by mutual bond a carbon chain having 2 to 13 carbon atoms or its side chain substituent; X and X' are each independently hydrogen atom or —CONH— radicals; $M^+$ is a cation, and x, y and z are values indicating the relative molar proportions of the respective corresponding units and complying with the required normalizations: $x+y+z=1$ and $0.1 \leq 100x/(x+y+z) \leq 100$. The α-carbon in $R_2$ radical is directly bonded with the carbon atom of the carboxylate radical, $-COO^-M^+$.

The carboxylate urea compound as given by the aforesaid general formula may be classified into four types as follows:

(1) Where $x=1$, $y=0$ and $z=0$, that is, component x alone is present;

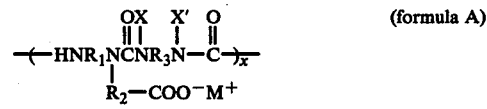

(2) Where $z=0$, that is, components x and y are present;

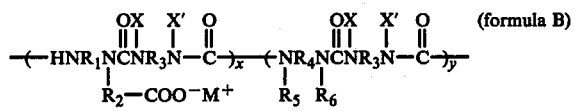

where $x+y=1$, and $0.1 \leq 100x/(x+y) < 100$.

(3) Where $y=0$, that is, components x and z are present;

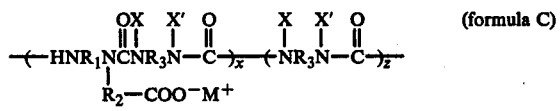

where $x+z=1$, and $0.1 \leq 100x/(x+z) < 100$.

(4) Where components x, y and z are all present;

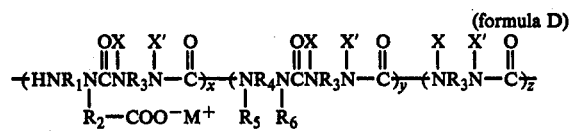

where $x+y+z=1$, and $0.1 \leq 100x/(x+y+z) < 100$.

It should be noted that each of the general formulae A to D merely indicates the components, compositions or structures of each unit, but is not intended to define the configuration or the direction of each unit.

While X and X' are hydrogen atoms or —CONH— radicals representing amide bonds, the molar ratio of the —CONH— radical should preferably accounts for 30% or less over the total molar amounts of X and X', because too many biuret bonds, as compared with hydrogen bonds, may cause intermolecular cross-linkages that will lead to gelation and the like, thereby reducing the utility value of the product: e.g., the resultant polymer tends to be thermosetting.

The term "hydrocarbon-based radical" as mentioned herein and in the appended claims is a generic expression of hydrocarbon radicals (aliphatic, alicyclic, aliphatic-substituted alicyclic, aromatic, aliphatic-substituted aromatic, alicyclic-substituted aromatic, and aliphatic-substituted alicyclic-substituted aromatic radicals) and substituted hydrocarbon radicals substituted and non-hydrocarbon radicals (e.g., halogen, cyano radical, etc.) which do not react with other starting materials and not inhibit or retard the intended reaction.

DETAILED DESCRIPTION OF THE PREFERRED EMBODIMENTS

In the above formulae, $R_1$ is a divalent residual radical derived from the elimination of the two amino groups from primary diamines known in the art. Such diamines include aliphatic diamines having 2 to 17 carbon atoms such as ethylenediamine, trimethylenediamine, tetramethylenediamine, hexamethylenediamine, heptadecamethylenediamine, 1,2-diaminopropane, 2,2,4-trimethylhexamethylenediamine and the like; alicyclic or aliphatic-substituted alicyclic diamines having 6 to 15 carbon atoms such as 1,3-diaminocyclohexane, 1,4-diaminocyclohexane, 1,3-diamino-1-methylcyclohexane, 3,5-diamino-1,1$^1$-dimethylcyclohexane, 1,5-diamino-1,3-dimethylcyclohexane, 3,1$^1$-diamino-1-methoxyethylcyclopentane, 1,5-diamino-1-methyl-3-methoethylcyclohexane, 1,4$^1$-diamino-1-methyl-4-methoethylcyclohexane, 1$^1$,3$^2$-diamino-1-methyl-3-dimethoethylcyclopentane, 4,4'-diaminodicyclohexylmethane and the like; aromatic or aliphatic-substituted aromatic diamines such as m-phenylenediamine, p-phenylenediamine, 4-methylphenylenediamine-(1,3), 2-methylphenylenediamine-(1,3), 3-aminobenzylamine, 4-aminobenzylamine, 4-amino-β-phenethylamine, p-xylylenediamine, 4,4'-diaminodiphenylmethane, 3,3'-dichloro-4,4'-diaminodiphenylmethane. Further, $R_1$ may contain a functional radical(s) which does not react with either amine or isocyanato radicals nor retard or inhibit the polymerization reaction thereof. Examples of diamines containing such $R_1$ radical are halogen-substituted aromatic diamines, ω,ω'-diamino-polyether and ω,ω'-diamino-polyester, the latter two polymer diamines having a repeating unit of 2 to 20 carbon atoms and an average molecular weight of 10,000 or less and preferably 104 or more.

$R_2$ is ethylene radical and an ethylene-based radical in which ethylene radical is substituted with a hydrocarbon radical(s) or a functional radical(s) such as formamido, acetamido, phthalimido, methoxy, ethoxy, halogen and the like radicals which do not react with isocyanato or amino radical. Examples of $R_2$ are ethylene radical; α-substituted ethylene radicals such as α-methylethylene, α-ethylethylene, α-phenylethylene, α-formamidoethylene, α-acetamidoethylene, α-phthalimidoethylene, α-methoxyethylene, α-ethoxyethylene, α-chloroethylene, α-bromoethylene, α-cyanoethylene, α-acetoxyethylene and the like radicals; α,α-disubstituted ethylene radicals such as α,α-dimethylethylene, α,α-bis(chloromethyl)ethylene, α,α-diacylamidoethylene and the like radicals; α,β-disubstituted ethylene radicals such as α,β-dichloroethylene, α-methyl-β-chloroethylene, α-cyano-β-phenylethylene and the like radicals; and β-substituted ethylene radicals such as β-methylethylene, β-phenylethylene, β-ethoxyethylene, β-chloroethylene and the like radicals.

$R_3$ is a divalent residual radical derived from the elimination of the two isocyanato radicals from diisocyanates which are commonly used as a starting material for well known polyurethanes or polyureas and constitute the starting material in this invention. Such diisocyanates include aliphatic diisocyanates having 4 to 16 carbon atoms such as butane-1,4-diisocyanate, hexane-1,6-diisocyanate, nonane-1,9-diisocyanate, 2-methylbutane-1,4-diisocyanate, dimethylsilanediisocyanate and the like; alicyclic diisocyanates having 8 to 20 carbon atoms such as cyclohexane-1,3-diisocyanate, cyclohexane-1,4-diisocyanate, 1-ethylcyclohexane-2,4-diisocyanate, dicyclohexylmethane-4,4'-diisocyanate, ω,ω'-1,4-dimethylcyclohexanediisocyanate and the like; aliphatic-substituted aromatic diisocyanates having 9 to 20 carbon atoms such as 4-phenylisocyanate-methylisocyanate, 4-phenylisocyanate-β-ethylisocyanate and the like; alicyclic-substituted aromatic diisocyanates having 12 to 20 carbon atoms such as tetrahydronaphthylene-1,5-diisocyanate, hexahydrodiphenylmethane-4,4'-diisocyanate and the like; and aromatic diisocyanates having 8 to 25 carbon atoms such as 1,3-phenylenediisocyanate, 1,4-phenylenediisocyanate, 1-methylbenzene-2,4-diisocyanate, 1-methylbenzene-2,6-diisocyanate, naphthalene-2,7-diisocyanate, diphenylmethane-4,4'-diisocyanate and the like. In addition, isocyanato-terminated polyester and polyether having an average molecular weight of 10,000 or less and preferably 302 or more obtained by a well known technique are also included.

$R_4$, $R_5$ and $R_6$ are residual radicals derived from the elimination of the amino radicals from the diamines represented by the formula:

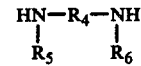

Such diamines include aliphatic secondary and primary-secondary diamines having 3 to 28 carbon atoms such as N-methylethylenediamine, N-ethylethylenediamine, N-propylethylenediamine, N-methyltetramethylenediamine, N-(δ-chlorobutyl)pentamethylenediamine, N-methylhexamethylenediamine, N-ethylhexamethylenediamine, N-propylhexamethylenediamine, N-isobutylhexamethylenediamine, N,N'-dimethylethylenediamine, N,N'-diethylethylenediamine, N,N'-dimethyltetramethylenediamine, N,N'-dimethylhexamethylenediamine, N,N'-diethylhexamethylenediamine, 1,10-bis-octylamino-2,9-dimethyldecane and the like; alicyclic secondary and primary-secondary diamines having 5 to 26 carbon atoms such as N-methyl-1,4-diaminocyclohexane, N,N'-dimethyl-1,4-diaminomethylcyclohexane, piperazine, 1,4-diazacycloheptane, 1,15-diazacyclooctacosane and the like; aromatic secondary and primary-secondary diamines having 7 to 21 carbon atoms such as N-methyl-m-phenylenediamine, N,N'-dimethyl-m-phenylenediamine, N-ethyl-m-phenylenediamine, N,N'-diethyl-m-phenylenediamine, N-methyl-p-phenylenediamine, N,N'-dimethyl-p-phenylenediamine, N-ethyl-p-phenylenediamine, N-propyl-p-phenylenediamine, N,N'-dimethyl-4-methylphenylenediamine-(1,3), N,N'-dimethyl-2-methylphenylenediamine-(1,3), N,N'-dimethyl-4,4'-diaminodiphenylmethane and the like, as well as the diamines mentioned with respect to $R_1$ radical. Further, polyamines in which the total of the numbers of primary and secondary amino groups is 2 and the other amino groups are tertiary are included, such as 1-(2'-aminoethyl)piperazine, 1,4-di(2'-aminoethyl)piperazine and the like.

Examples of M are alkali metals such as lithium, sodium, potassium and the like; alkaline earth metals such as magnesium, calcium, strontium, barium and the like; and tertiary amines such as trimethylamine, dimethylethylamine, triethylamine, dimethylpropylamine, dimethylisopropylamine, methylethylpropylamine, methyldipropylamine, methylpropylbutylamine, pyridine, N-methylmorpholine, N,N-dimethylaniline, triethylenediamine and the like. However, M is not limited to these examples. Generally, M is a basic substance which can form a carboxylate salt and whose corresponding cation $M^+$ does not react with an isocyanate.

X and X' have already been described hereinabove.

The carboxylate urea compound of the invention may be prepared by reaction of aminoaminocarboxylate expressed by the general formula:

with diisocyanate expressed by the general formula:

optionally in the presence of diamine represented by the formula:

and/or water. If aminoaminocarboxylate (formula I) and diisocyanate (formula II) alone are allowed to react, there will be obtained a compound as given by formula A. Meanwhile, if such reaction is accompanied by the addition of diamine (formula III) or water, then there will be obtained a compound as given by formula B or C, respectively. As a matter of course, if the reaction is conducted with addition of both diamine and water, there will be produced a compound as given by formula D.

Aminoaminocarboxylic acids or salts thereof (formula I), one of the starting materials in the invention, may be obtained by the reaction of, for example, β-propiolactone with diamine as shown in Kogyo-kagaku Zasshi 73, 1720 (1970) by S. Katayama; S. Horikawa and M. Ohbuchi. $R_1$ and $R_2$ have already been described hereinabove. Examples of aminoaminocarboxylic acid are aliphatic aminoaminocarboxylic acids having 5 to 21 carbon atoms such as N-(2-carboxyethyl)-ethylenediamine, N-(2-carboxyethyl)-trimethylenediamine, N-(2-carboxyethyl)-hexamethylenediamine, N-(2-methyl-2-carboxyethyl)-hexamethylenediamine and the like; aliphatic-substituted alicyclic aminoaminocarboxylic acids having 9 to 19 carbon atoms such as N-(2-carboxyethyl)-1,4-diaminocyclohexane, 3-N-(2-carboxyethyl)-1,3-diamino-1-methylcyclohexane, N-(2-carboxyethyl)-4,4'-diaminodicyclohexylmethane and the like; and aliphatic-substituted aromatic aminoaminocarboxylic acids having 9 to 19 carbon atoms such as N-(2-carboxyethyl)-p-phenylenediamine, N-(2-carboxyethyl)-p-xylylenediamine, N-(2-methyl-2-carboxyethyl)-p-xylylenediamine, N-(2-carboxyethyl)-4,4'-diaminodiphenylmethane, N,N'-di(2-carboxyethyl)-3,3'-dichloro-4,4'-diaminodiphenylmethane and the like.

These aminoaminocarboxylic acids may be used in the form of aminoaminocarboxylates neutralized with a prescribed base M and isolated prior to the preparation of the carboxylate urea compound, or as another method aminoaminocarboxylic acid is neutralized with the base M and used without isolation for polymerization to give the urea compound.

Typical examples of diisocyanate (formula II) and diamine (formula III) are as previously described.

The carboxylate urea compound of the invention may be obtained by interfacial polymerization, solution polymerization, and solvent-free polymerization as hereinafter described in detail. Aminoaminocarboxylate, diamine, and water may, if desired, be previously mixed before the polymerization reaction because they would not react with one another in any case.

In the reaction of primary or secondary amino radical(s) with isocyanato radical(s), polymerization catalysts are not necessarily required since the reaction usually proceeds at a considerable rate. When accelerating the polymerization rate or using weakly basic aromatic diamines, however, catalysts should preferably be employed. Such catalysts are known in the art as used in the production of polyurethanes and polyureas, and include tertiary amines such as triethylamine, N-methylmorpholine, N,N,N',N'-tetramethylpropyldiamine, N,N,N',N'-tetramethyl-1,3-butanediamine, N,N,N',N'-tetramethylhexamethylenediamine, N,N-dimethylbenzylamine, N,N-dimethyllaurylamine, N,N'-dimethylpiperazine, triethylenediamine and the like; tin compounds such as tributyl tin acetate, dibutyl tin diacetate, dibutyl tin dilaurate, dibutyl tin sulfide, dibutyl tin dichloride, stannic chloride, stannous octoate, stannous oleate and the like; lead compounds such as lead benzoate, lead oleate and the like; cobalt compounds such as cobalt-2-ethylhexoate, cobalt naphthenate, cobalt benzoate and the like; zinc compounds such as zinc naphthenate, zinc-2-ethylhexoate and the like; carboxylic acids such as n-butyric acid, valerianic acid and the like; and ureas such as N-phenyl-N'-o-tolylurea. Not useable, however, are those which react with amines to produce substances that may destroy carboxylate structure, or to inactivate their own catalytic actions; such as chlorocarboxylic acid, hydrogen chloride, sulfuric acid, etc. If component z originating from water in the aqueous interfacial polymerization as mentioned later is desired to be minimized catalysts can be employed that may selectively accelerate the reaction between the isocyanate and amino radicals rather than the reaction between the isocyanato radical and water. These catalysts include stannous octoate and N-ethylmorpholine, for example. On the other hand, dibutyl tin diacetate, tributyl tin acetate, triethylenediamine, etc. will acclerate the reaction with water to increase component z. Further, dibutyl tin dilaurate is an intermediate of these two types.

While the carboxylate urea compounds of the invention, as already described, include also those with branched or cross-linked structure resulting from the formation of partial biuret bonds due to the reaction of N-hydrogen radical of urea bond with isocyanato radical, production of such branched or cross-linked structure may be facilitated by such catalysts as dibutyl tin diacetate, tributyl tin acetate, and triethylenediamine, which accelerate the ureaisocyanato reaction. Accordingly, if such branched or cross-linked structure is not desired, these catalysts are not used. As the catalysts to accelerate the formation of biuret bonds, there are tin compounds such as dibutyl tin diacetate and tributyl tin acetate; triethylenediamine; the aforesaid zinc compounds, etc.

Many of the aminoaminocarboxylates as given by formula I and their corresponding aminoaminocarboxylic acids generally have a high melting point, and dissolve in highly polar protic solvents, such as water and low carbon alcohols, as well as in highly polar solvents having high dielectric constant, such as N,N-dimethylformamide and dimethylsulfoxide, though they are hardly soluble in other low polar solvents. However, aminoaminocarboxylic acid having lower ionic density, that is, having higher molecular weight has a lower melting point and higher solubility. Therefore, the polymerization method and conditions should be selected in accordance with the melting point and solubility of the aminoaminocarboxylic acid or its salt (formula I).

When using protic solvents such as water, etc., polymerization can be conducted if the reactivity of aminoaminocarboxylate (formula I) is sufficiently higher than that of the protic solvents or if there is used any of those catalysts which preferentially acclerate the reaction with amino radicals as aforesaid. Also, polymerization can be achieved in case there is applied the so-called interfacial polymerization method in which diisocyanate (formula II) is dissolved in a nonpolar solvent immiscible with the protic solvents, aminoaminocarboxylate (formula I) is dissolved in a protic solvent, and the resultant two solutions are mixed with each other, and then polymerization takes place at the interface.

Most widely used are polar aprotic solvents such as dimethylformamide and dimethylsulfoxide. A solution of aminoaminocarboxylate (formula I) for the polymerization with diisocyanate (formula II) may be prepared by dissolving aminoaminocarboxylic acid and a base M in these solvents, or as another method by dissolving aminoaminocarboxylate (formula I) directly in these solvents. In preparation of the solution of the aminoaminocarboxylate, however, if the base M, like the hydroxides of alkali metals or alkaline earth metals, gives by neutralization water or other low molecular weight substances in the former case, the low molecular weight substances may react with the isocyanato radical to interfere with the polymerization, or produce component z when the low molecular weight substance is water. The latter case has no such inconvenience, but has other disadvantages such as: increase of steps of preparing process due to the additional previous preparation of aminoaminocarboxylate (formula I) and generally poorer solubility and operability of aminoaminocarboxylate (formula I) as compared with the former case. Further, a polymer electrolyte of the invention is generally applied in the form of an aqueous solution, which can be directly prepared by the aforesaid aqueous interfacial polymerization method. According to the solution polymerization method, however, the aqueous solution can be obtained only by dissolving in water the polymer electrolyte has been isolated by precipitation in a non-solvent. Meanwhile, if the object is to obtain a formed product of the polymer electrolyte by the dry or wet process, the solution polymerization method is advantageous in that the formed product may easily be obtained by the evaporation of the polar aprotic solvent or by extruding the polymer electrolyte solution in a nonsolvent.

Solvent-free polymerization is performable if the melting point of aminoaminocarboxylate (formula I) is low or its amine value is small, that is, for example, if $R_1$ in formula I contains any ether bond or if $R_1$ is selected from any of a considerably long-chain aliphatic hydrocarbon radical having a low melting point, polyether and polyester radicals. Meanwhile, with a large amine value, the solvent-free polymerization can be carried out by admixing a filler which does not react with either isocyanato or amino radicals. This filler is not the aforesaid solvent but a substance which is not necessarily required to dissolve the aminoaminocarboxylate (formula I) and diisocyanate (formula II) and can produce a polymer mixture containing it to exhibit satisfactory properties as a high molecular weight composite. Typical examples of such diluting filler which would not react with diamine and diisocyanate include inorganic materials such as calcium carbonate, glass fiber, ceramic wool, rock wool, fine gravel, perlite, silica, alumina, silica balloon, glass balloon, barium sulfate, etc.; organic materials such as wood, pulp, natural or synthetic fibers, waste paper, fragments of plastics, etc.; and metal powder such as iron powder, copper powder, aluminum powder, etc.

Even with a large amine value, foamed products may be produced by high-speed exothermic reaction if the melting point of aminoaminocarboxylate (formula I) is low. The solvent-free polymerization may be performed by mixing aminoaminocarboxylate (formula I) with diisocyanate (formula II) in the presence or absence of any fillers as occasion demands, polymerizing them at a proper temperature for a suitable period of time, and preferably curing the product at a higher temperature to further complete polymerization. Although such solvent-free polymerization is advantageous in that a formed product can be produced by one step, it has a defect that it is difficult to prepare thermoplastic or soluble polymers.

While the polymerization temperatures for the aforementioned polymerization in protic solvent (e.g., aqueous interfacial polymerization), polar aprotic solution polymerization, and solvent-free polymerization may vary with the situations, it is desired that a relatively low temperature should be used at the initial stage in any of these cases. This is because it is desired that the initial molecular weight of the polymer is sufficiently increased to obtain satisfactory properties of a high molecular weight substance by giving priority as much as possible to the production of urea bonds resulting from the reaction of aminoaminocarboxylate (formula I), as well as diamine (formula III) used at need, with diisocyanate (formula II). In preparing foamed products by high-rate polymerization, however, foaming is performed by taking advantage of the production of heat due to the rapid deposition of polymerization heat, regardless of initial temperature, so that cross-linking reaction may be caused as a side reaction, usually rendering the so-called initial or primary molecular weight not very high, though it is sufficient for the properties of a foamed product. As the polymerization temperature elevates, the significant differences between the reactions of the amino radical, water, and urea bond on the isocyanate radical are reduced, hardly increasing the primary molecular weight, and the component z may often increase when water is used or cross-links increase. Addition of a catalyst may cause the significant difference in the selective reactivity of the active protons, such as amino radicals, urea radicals, and water, with the isocyanato radical reduced, depending on the kind of catalyst. Therefore, it is desired that the catalystless reaction should be employed for the initial stage of polymerization, and the catalyst should be added after the reaction between the amino and isocyanato radicals has been fully carried out. The reason is that the catalystless reaction may often take advantage of the normal relation amino radical > water $\geq$ urea as regards the reactivity with the isocyanato radicals. The reaction of a small amount of remaining isocyanato radicals can be completed by elevating the polymerization temperature at the end of the polymerization, that is, at the time when most of the isocyanato radicals have finished reaction. In this case, the aforesaid competing reaction, if any, will hardly have a bad influence on the properties of the polymer, but, on the contrary, increase the molecular weight and eliminate the harmful effects attributable to the remaining isocyanato radicals. In general, polymerization with protic solvents should preferably be performed at a low temperature; the aprotic solution polymerization may of course be performed at a relatively high temperature, and the solvent-free polymerization may be done in ranges of both high and low temperatures.

While the common features and advantages of the preparing method of this invention have been described above, there will now be described in detail the interfacial polymerization, solution polymerization, and solvent-free polymerization methods.

Interfacial Polymerization

The solvents mainly used in the interfacial polymerization method are water and organic solvents insoluble in water. The latter may be any organic solvents which dissolve diisocyanate (formula II) and do not or react very slowly with isocyanato radicals, including aliphatic hydrocarbons, or halides or sulfides thereof, such as cyclohexane, chloroform, methylene chloride, carbon tetrachloride, 1,2-dichloroethane, tetrachloroethylene, carbon disulfide, etc.; and aromatic hydrocarbons, or halides or nitro derivative thereof, such as benzene, xylene, chlorobenzene, dichlorobenzene, nitrobenzene, etc., though these are given only by way of examples. Strictly speaking, the interfacial polymerization should be called interfacial polyaddition reaction, which is different from the so-called interfacial polycondensation reaction in which the conventional Schotten-Baumann reaction is utilized. One of the greatest differences between these two reactions is that in the interfacial polycondensation alkali is added to the aqueous system for neutralization in order to remove hydrogen chloride or other low molecular by-products and direct the equilibrium of reaction toward the polymer production. Typical examples of such addition of alkali are performed in preparation of polyamide by the interfacial polycondensation reaction of dibasic acid chloride and diamine, preparation of polyurethane by the interfacial polycondensation reaction of dichloroformic ester and diamine, or preparation of polyphenyl ester by the interfacial polycondensation reaction of dibasic acid chloride and bisphenol, for example. The interfacial polycondensation reaction is an equilibrium reaction in which polymerization does not proceed unless the low molecular by-products are removed, while in the interfacial polyaddition reaction, which is not such an equilibrium reaction, alkali is not required to be added because no low molecular products are formed. In polymerization the aminoaminocarboxylate (formula I) and diamine (formula III) (if required) are dissolved in water, while the diisocyanate (formula II) is dissolved in the aforesaid organic solvent that is immiscible with water. The proper solution of aminoaminocarboxylate (formula I) may also be prepared by dissolving the aminoaminocarboxylic acid and base M in the polar solvent for neutralization instead of directly dissolving the aminoaminocarboxylate (formula I) in the polar solvent.

Although concentrations of the reactants in the solvents may be selected rather voluntarily, it is advisable that the concentrations of aminoaminocarboxylate (formula I) should be relatively high in order to prepare carboxylate polyurea with high density of electric charge. Usually, these concentrations have an maximum limit at such a level that enables stirring of the produced polymer solution or emulsion. However, higher viscosity may retard the polymerization or cause uneven polymerization, so that the proper concentration may range from 0.1% to 40%, preferably from 1% to 30%.

Although the maximum limit of the polymerization temperature is 100° C. because of the aqueous system being used, actual polymerization will be performed below the boiling point of a particular organic solvent used if such solvent boils at a temperature lower than 100° C. Meanwhile, if the temperature is elevated as stated above, then the z-components of the carboxylate polyurea will be increased largely due to the reaction of the water with diisocyanate (formula II), and the x-components, i.e., carboxylate components may be reduced or hydrolysis may be involved. Therefore, it is advisable to perform the polymerization usually at about 60° C. or below. Although the minimum limit of the polymerization temperature should only be higher than the freezing temperature of the aqueous solution, it frequently drops below 0° C. due to the freezing point depression attributable to the existence of the aminoaminocarboxylate (formula I) and diamine (formula III). However, if the freezing point of the organic solvent is higher than 0° C., as is the case with, for example, benzene, and the concentration of the solution is too low to cause freezing point depression down to 0° C., then the polymerization should be carried out at a temperature higher than 0° C. After all, the main polymerization reaction should be performed preferably at a temperature ranging from the freezing point of the polymerization system to 60° C., most preferably from 0° C. to 35° C.

While the objective carboxylate polyurea having satisfactory high molecular property may be obtained by the main polymerization reaction in which reaction of most of the isocyanato radicals present is completed, it is desired that curing should finally be performed at a somewhat elevated polymerization temperature in order to complete the reaction of the small amount of remaining isocyanato radicals as aforesaid. In doing this, heating is usually performed at a temperature 5° to 30° C. higher than the main polymerization temperature. Further, as previously described, polymerization may be accelerated by the addition of such catalysts as stannous octoate and N-ethylmorpholine that selectively accelerate the reaction of amino radicals with isocyanato radicals and hardly have any effects on the reaction between isocyanato radicals and water. Although such catalysts may be added at an initial stage of the main polymerization reaction, it is most advisable to add them at the end of the main polymerization, that is, at the time when most of the isocyanato radicals have finished reaction and then to continue polymerizing at the same temperature in order preferably to avoid the side reactions as already mentioned. In preparing polymers with intentionally increased z-components, water-insoluble polymers, or cross-linked polymers, the final purpose can be attained by adding at the initial stage of the main polymerization reaction triethylenediamine, tetramethyl-1,3-butanediamine, dibutyltindilaurate or other catalysts that affect on the reaction between isocyanato radicals with water, as well as the above-mentioned catalysts.

Thus obtained reaction product may be isolated or refined by the following methods, for example. Since hardly any carboxylate polyurea exists in the organic solvent phase because of its high-polarity, the aqueous solution phase containing the product may be obtained by separating and removing the organic solvent phase by decantation or by means of a separating funnel when aqueous and organic-solvent phases are separated in layers from each other. While the aqueous solution of the carboxylate polyurea may be cleared of some remaining organic solvent by evaporation, and used directly as a product, a carboxylate polyurea may, if necessary, be also isolated by precipitation as mentioned later. If there exists any water-insoluble polymer, it should only be previously isolated by filtration. If the reaction mixture is in the form of emulsion, suspension, paste, or cream, prohibiting the aforesaid layer separation, the organic solvent is removed by heating the mixture under reduced pressure, and then the aforementioned treatment is performed. If there can be obtained no uniform phase for all that, the carboxylate polyurea can be isolated by evaporating a proper amount of water as well as the organic solvent to concentrate the reaction mixture and then adding the resultant concentrate to a solvent soluble in water but incapable of dissolving carboxylate polyurea for precipitation. Since the isolated substance may contain both water-soluble and water-insoluble components, an aqueous solution composed of the water-soluble component alone may be obtained by again dissolving both these components in water and filtering out the insoluble portion in order to separate these components from each other. While solution thus obtained may be offered directly as a final product as aforesaid, water-soluble carboxylate polyurea can be isolated by precipitation, if required. In precipitation the aqueous solution may be added directly to the precipitation solvent, or as another method the aqueous solution is dried up to be free from water and dissolved in any other solvent, such as polar aprotic solvents used in the solution polymerization as described hereinafter and polar protic solvents including alcohols, formic acid, formamide, m-cresol, etc. depending on the types of carboxylate polyurea, the resultant solution being added to a precipitation solvent for precipitation. The precipitation solvent may be selected from nitriles such as acetonitrile and propionitrile; ketones such as acetone and methyl ethyl ketone; ethers such as diethyl ether, dioxane, and tetrahydrofuran; and esters such as ethyl acetate. The precipitation solvent, however, is not limited to the aforesaid substances, but may be found among solvents that have permanent dipoles hardly capable of free rotation and can never or hardly dissolve the carboxylate polyurea. Non-polar solvents or polar solvents having free-rotatable chemical bonds tend to produce gummy or oily substances.

Solution Polymerization

Polar aprotic solvents are preferred in the solution polymerization because the electrolyte, that is, carboxylate polyurea may hardly be dissolved in solvents having low-polarity and also because aprotic solvents having no active hydrogens are required to minimize the reaction between the isocyanato radicals and the solvent. Such aprotic solvents include tertiary amides such as N,N-dimethylformamide, N,N-dimethylacetamide, and N-methylpyrrolidone; aprotic organic sulfur oxides such as dimethylsulfoxide; and triesters of phosphoric acid such as triethyl phosphate and tri-n-butylphosphate. Aminoaminocarboxylate (formula I) having low density of electric charge or some lithium salt may, however, hardly be dissolved even in the above-mentioned polar solvents. In such a case the solubility may be improved by adding some electrolytes that do not react with diisocyanate (formula II) but dissolve in the polar solvents. Such electrolyte may be selected from salts such as fluorides, chlorides, perchlorates and nitrates of alkali metals including lithium, sodium, and potassium; zinc chloride; mercury chloride, alkaline metal alcoholates such as lithium methylate, sodium methylate, and potassium ethylate; salts such as halide, perchlorate, tetrafluoroborate, nitrate, acetate and sulfonate of tetraalkylammonium; tetrarylborates such as tegraphenylborate, for example.

While in polymerization the aminoaminocarboxylate (formula I) is dissolved in the aforesaid polar solvent, any aforesaid electrolyte may be added as the solubilizing agent, if necessary. In doing this, the electrolyte solubilizing agent is added at a level below its saturation solubility in the polar solvent, but adding a little amount of solubilizing agent may be enough because such solubility is usually low. Diamine (formula III) may be added, if required, to the solution of aminoaminocarboxylate (formula I). The proper solution of aminoaminocarboxylate (formula I) may also be prepared by dissolving the aminoaminocarboxylic acid and base M in the polar solvent for neutralization instead of directly dissolving the aminoaminocarboxylate (formula I) in the polar solvent. In this case, however, water may sometimes be produced by the neutralization as aforesaid. The water may be removed by addition of any conventional dehydrating agent which does not react with the aminoaminocarboxylate (formula I), diisocyanate (formula II) and diamine (formula III) and carboxylate polyurea. Such dehydrating agent may be selected from sodium sulfate, magnesium sulfate, calcium sulfate, copper sulfate, aluminum sulfate, alumina, and silica gel, for example. Although the diisocyanate (formula II) may be added directly to the solution, it may cause a sudden exothermic reaction if the concentration is high or the basicity of the amine component is strong. This may be avoided by diluting the diisocyanate (formula II) with the polar solvent and adding it gradually to the solution of amine component.

Although the polymerization may be performed in the air, it should preferably be done in an inert-gas atmosphere of dehumidified atmosphere in order to minimize the denaturing of diisocyanate, aminoaminocarboxylate (formula I) and/or diamine (formula III) by carbon dioxide and water in the air.

Although the polymerization temperature may be at any level higher than the freezing point and lower than the boiling point of the polymerization system, higher temperature is liable to cause production of the aforementioned biuret bonds due to the reaction between the urea bonds and isocyanato radicals as well as accompanying side reactions such as cross-linking reaction. Therefore, the polymerization should be performed usually at a temperature below 200° C., preferably above the freezing point and up to 100° C. Practically, in order to minimize the side reactions, the first stage polymerization is performed at a relatively low temperature, e.g., the normal temperature (20° C.), and the second stage polymerication is started after most of the isocyanato radicals have reacted. In the second stage polymerization, the reaction temperature may be substantially the same as that of the first stage, though the polymerization reaction is further completed by the addition of a catalyst for accelerating the reaction between the aforesaid isocyanato and amino radicals. If the second stage polymerization cannot yet provide a high molecular weight polymer, leaving a small amount of isocyanato radicals, it is advisable to perform third stage polymerization at a temperature 5° to 100° C. higher than those of the first and second stages. Not all these three stages of polymerization are required; the first stage alone may often be enough when the polymerization rate is high, or aromatic diisocyanate and aliphatic diamine reactants react with each other, or if high concentration of the reactants is used for the reaction. The first stage of polymerization may be directly followed by the third stage, or otherwise the second stage reaction may be firstly carried out in the case with very slow polymerization rate. In a reaction system with high polymerization rate, however, it is not desired from a point of view of side reactions to start the second or third stage of polymerization, neglecting the first stage polymerization.

If the polymerization is performed under the above-mentioned conditions, it will be completed within a period of time ranging from a few minutes to approximately 10 hours. Although the reactant concentration may be any any level that allows the reaction system to be stirred or kneaded, low concentration will retard the polymerization or reduce the yield. On the other hand, too high concentration has the advantage to accelerate the polymerization rate, but has the disadvantage to cause side reactions such as cross-linking reaction giving impure polymer compositions. Accordingly, the polymerization should usually be performed with a reactant concentration of 1% to 50%, most preferably 5% to 30%.

While a solution of the thus obtained carboxylate polyurea may be used as it is depending on the application, the polymer itself may be isolated by precipitation using the aforesaid precipitation solvent. Further, films may be manufactured by heating and evaporating the solvent (dry process), while films or fibers may be manufactured by discharging the solution into a non-solvent (wet process).

Solvent-free Polymerization

The solvent-free polymerization method may be applied to the case in which the aminoaminocarboxylate (formula I) has a low melting point or its amine value is small, or a mixture of the aminoaminocarboxylate and diamine (formula III) has a low melting point or small amine value, as well as to mixtures including the aforementioned fillers. In these cases, the polymerization is generally performed immediately after mixing the materials and pouring or filling the mixture into any suitable container or casting mold. Though catalysts are hardly required because the polymerization rate is usually high, they should suitably be used when using any fillers for dilution. The polymerization is carried out usually around the normal temperature, though cooling or heating may be effected as occasion demands. After the polymerization has nearly completed, the reaction system should preferably be heated at a temperature higher than the polymerization temperature at the first stage for a suitable period of time in order further to stabilize the properties of the polymer. The preferred temperature for the first stage of polymerization is usually 0° C. to 100° C., while the so-called curing temperature in the second stage ranges from 50° C. to 200° C. The polymerization time varies with the polymerization temperature, filling material, and the reactant; 30 minutes to 30 hours for the first stage of polymerization, and 0 to 30 hours for the curing reaction of the second stage.

The carboxylate polyurea of this invention as a polymer electrolyte has the following distinguished properties.

(a) Water-solubility or hydrophilic property.
(b) Flocculation.
(c) Never changes the surface tension.
(d) Moisture- and water-absorptive properties.
(e) Antistatic property.
(f) Ionizability.
(g) Ability to chelate with metals.
(h) Ion-exchangeability.
(i) Buffer action.
(j) Low dielectric property though having the polar radical.
(k) Safety to organisms.

All these properties except the one given by (k) are entirely attributable to the characteristic effects owing to the existence of x-component; some properties are found more definitely with higher rate of x-component, and others indicate optional improvement of the conventional polyureas or other components caused by the addition of x-component.

Taking advantage of the above properties the polyurea of this invention may be used for a wide variety of applications including antistatic agents, dye fixing agent, flocculants, sensitizers, photosensitive agents, auxiliaries for ink or paints, ion-exchange resins, adsorbents, chelating agents, electrodeposition paints, water-soluble adhesives, reactive paints, non-pollutional agricultural chemicals, cosmetic materials, dielectrics, oxidants and reductants, pH controllers, soil conditioners, etc.

This invention will be more fully understood from the following Examples. In these Examples diamines with radical $R_1$ are selected only from aliphatic, aliphatic-substituted aromatic, and aromatic diamines, and diisocyanates with radical $R_3$ are selected only from aliphatic, aliphatic-substituted aromatic, and aromatic diamines. Hereupon, according to the invention, it has been found that the reactivity of these diamines is subject to a relation: aliphatic < aromatic, while that of these diisocyanates is subject to a relation: aromatic < aliphatic, the reactivity of compounds of other groups being intermediate between those of aromatic and aliphatic compounds.

EXAMPLES 1 to 5

5.00g (0.038 mol) of N-(2-carboxyethyl) ethylenediamine (m.p.: 130° to 136° C., hereinafter referred to as CEED) and a solution of 1.44g (0.036 mol) of sodium hydroxide (this corresponds to the equivalent calculated from the measured value of the acid equivalent of CEED) in a quantity of degassed distilled water as shown in Table 1 were placed in a four-necked pear-shaped separable flask (200ml capacity) equipped with a dropping funnel with a side arm working as a nitrogen inlet, a condenser working as a nitrogen outlet, a thermometer and a stirrer, and were purged with nitrogen and stirred while keeping the flask at 20° C. in a water bath. A quantity of diisocyanate corresponding to the isocyanato radical/amino radical index calculated from the measured value of the base equivalent of CEED and shown in Table 1 was dissolved in a quantity of methylene chloride as shown in Table 1, and the resultant solution was gradually dropped into the stirred solution through the dropping funnel. After completion of such dropping, the solution was further stirred for reaction at the same temperature and then at a higher temperature. The reaction product was separated into three layers; an aqueous phase, an organic phase, and a portion soluble in neither of these phases. After the insoluble portion was filtered and separated, the aqueous and organic phases were separated from each other by means of a separating funnel or centrifuge. The aqueous phase was condensed or subjected to evaporation under reduced pressure, and then dissolved in methanol. The resultant solution was added to a fully stirred non-solvent for precipitation, and thus there was obtained colorless powder. Vacuum evaporation of the solvent of the organic phase gave an unreacted residue of diisocyanate. Table 1 shows the measurement results of yield, softening point, and intrinsic viscosity.

Referring now to Example 1, three will be described the method for analyzing the thus obtained water-soluble polymer. The water-soluble polymer exhibited asymmetric stretching vibration of carboxylate in a range 1,580 to 1,560 cm$^{-1}$ of the infrared absorption spectra, symmetric stretching vibration of carboxylic in 1,410 to 1,400 cm$^{-1}$, absorption of amide I in 1,640 to 1,620 cm$^{-1}$, and absorption of amide II in 1,550 to 1,530 cm$^{-1}$. Further, when this polymer was dissolved in heavy water and the nuclear magnetic resonance spectra were measured, the chemical shifts in δ value at a to d of formula (E) given by tively, so that the polymer was found to be a carboxylate polyurea having a composition given by $x=0.805$ and $y=0$. A small amount of water-insoluble portion had a composition given by $y=0$ and $z>>x$.

The water-soluble polymers of Examples 2 to 5 were found to be carboxylate polyureas with a composition given by $y=0$ and $77<100x/(x+z)<96$ as shown in Table 1. A small amount of water-insoluble portion had a composition given by $y=0$ and $z>>x$.

When the aqueous solutions of the polymers were added to solutions of the salts of copper, iron, cobalt and manganese, precipitation was produced, showing that the polymers have a chelating ability.

A film of 48μm thickness was obtained by dissolving the water-soluble polymer of Example 3 in methanol, pouring the resultant solution over a Teflon-coated iron plate, and drying at 40 to 50° C. The insulation resistance of this film was determined by subjecting the film to a measurement on the Model SM-10 Super-ultra Insulation Meter and Model SM-5E Ultra Insulation Meter (both from Toa Denpa Kogyo Co., Ltd.) in an atmosphere at 21±1° C. and 65±5% (relative humidity) and reading the values after 1 minute of operation of the meters. Thus, the surface inherent resistivity and volume inherent resistivity of the film were found to be 1.4 to $2.1 \times 10^{11}$Ω and 1.5 to $2.3 \times 10^{11}$Ω·cm, respectively, at 100V — sufficiently low electric resistance. Further, in the same atmosphere, a similar film placed on an earthed aluminium plate was subjected to a voltage of 15KV for 5 seconds by means of the Model KTB-5 charger (from Kasuga Denki Co., Ltd.) and measured on the Model KQ-431 Electrostatic Charge Meter (from Kasuga Denki), and the charge amount proved too small to be detected.

A flocculation test was performed for the water-soluble polymer of Example 3. About 2,300 ppm (pH7) of suspension of barium sulfate in water was used for the subject liquid. This suspension was placed in a 25ml tapped messcylinder and added with 0.1 wt% solution of water-soluble polymer. After the messcylinder was overturned ten times, it was allowed to stand, and the time required for the attainment of a constant sedimentation volume of the flock was measured. Consequently,

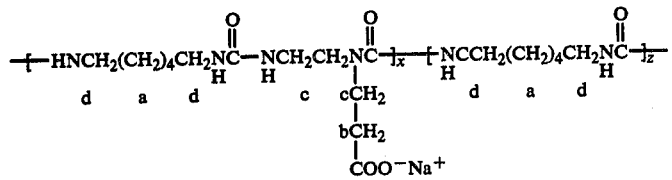

were as follows: a: 1.10 to 1.60 ppm; b: 2.30 to 2.44 ppm; and c+d: 2.96 to 3.50 ppm. These were multibullet signals. In order to obtain the components x and z in formula (E), the water-soluble polymer was dissolved in water, and subjected to titration by means of 0.1 N solution of hydrochloric acid to determine the carboxylate equivalent, and the component ratio of x was obtained according to the following equation.

$$x = \frac{\text{Observed value of carboxylate equivalent of polymer}}{\text{Calculated value of carboxylate equivalent of structure } x}$$

Hereupon, the observed value and calculated value of the carboxylate equivalent of the water-soluble polymer were $2.49 \times 10^{-3}$ eq/g and $3.10 \times 10^{-1}$ eq/g, respecthe sedimentation was started immediately after the messcylinder was allowed to stand, and completed within 3 minutes independently of the variation in the added amount of the polymer - 3, 6 and 12 ppm - and a cohesion effect was exhibited.

The same flocculation test was conducted for the water-soluble polymer of Example 4, and the greatest effect was attained with 3 ppm addition, completing the cohesion-sedimentation within 2 minutes.

In order to observe the surface active effect of the water-soluble polymer of Example 4, the surface tension was measured with varied concentrations of the polymer in water. There was employed the Denui's Surface & Interfacial Tension Meter (available from Shimazu Seisaku-sho Co., Ltd.) with the liquid temperature at 19.0° C. It was found that the surface tension hardly changes with the concentrations, as shown below.

| Concentration (wt %) | 0 | $5 \times 10^{-5}$ | $5 \times 10^{-4}$ | $5 \times 10^{-3}$ | $5 \times 10^{-2}$ | $5 \times 10^{-1}$ |
|---|---|---|---|---|---|---|
| Surface Tension (dyn/cm) | 70.6 | 68.9 | 69.1 | 69.2 | 70.6 | 67.0 |

Table 1
Conditions & Results of Synthesis of Carboxylate Polyurea

| Example | Diisocyanate: g (mol) | Index | Solvent (ml) Water | Solvent (ml) Methylene chloride | Reaction Temperature & Time (° C/min) Dropping agitation | Reaction Temperature & Time (° C/min) Agitation | | Yield (%) Water-Soluble portion | Yield (%) Water-insoluble portion |
|---|---|---|---|---|---|---|---|---|---|
| 1 | HMDI (i) 5.92 (0.035) | 1.0 | 70 | 50 | 20/30 | 20/40 | 50/150 | 56.0 | 6.8 |
| 2 | HMDI 7.10 (0.042) | 1.2 | 50 | 40 | 20/7 | 25/140 | 40/30 | 92.2 | 1.7 |
| 3 | HMDI 8.29 (0.049) | 1.4 | 30 | 30 | 20/8 | 20/170 | 40/150 | 76.9 | Very little |
| 4 | MDI (ii) 9.04 (0.036) | 1.0 | 50 | 50 | 20/40 | 20/30 | 40/30 | 82.9 | 9.0 |
| 5 | 2,4-TDI(iii) 8.59 (0.049) | 1.4 | 50 | 50 | 20/32 | 20/217 | 40/50 | 66.6 | 12.7 |

| Example | Softening point (° C) Water-soluble portion | Softening point (° C) Water-insoluble portion | Intrinsic viscosity (30° C, m-cresol) water-soluble portion (iv) | Precipitation solvent | Remarks |
|---|---|---|---|---|---|
| 1 | 100–110 | 215–220 | 0.143 | Precipitation by addition of methanol solution of the polymer to acetone | $x=0.805$ (Water-soluble portion) |
| 2 | 100–120 | 164–210 | 0.216 | " | $x=0.771$ (Water-soluble portion) |
| 3 | 169–184 | — | 0.334 | " | $x=0.771$ (Water-soluble portion) |
| 4 | 183–188 | 260–300 | 0.111 | Precipitation by addition of aqueous solution of the polymer to acetonitrile | $x=0.959$ (Water-soluble portion) |
| 5 | 230–235 | 234–247 | 0.105 | Precipitation by addition of methanol solution of the polymer to acetonitrile | $x=0.819$ (Water-soluble portion) |

NOTE:
(i) HMDI is hexane-1,6-diisocyanate.
(ii) MDI is diphenylmethane-4,4'-diisocyanate.
(iii) 2,4-TDI is 1-methylbenzene-2,4-diisocyanate.
(iv) Intrinsic viscosity was measured with concentration at 0.125g/25ml.
* Catalystless polymerization for Examples 1 to 5.

EXAMPLES 6 to 11

Employing the same apparatus as that of Example 1, a quantity of N-(2-carboxyethyl) hexamethylenediamine (m.p.: 107 to 113° C., hereinafter referred to as CEHD) as shown in Table 2 and a solution of a quantity of sodium hydroxide corresponding to the equivalent calculated from the measured value of the acid equivalent of CEHD in a quantity of degassed distilled water as shown in Table 2 were placed in the flask, purged with nitrogen, and stirred while keeping the flask at 20° C. in the water bath. A quantity of diisocyanate corresponding to the index calculated from the measured value of the base equivalent of CEHD and shown in Table 2 was dissolved in methylene chloride, and the resultant solution was gradually dropped into the stirred solution through the dropping funnel. After completion of such dropping, the solution was stirred for reaction at such temperature for such time as shown in Table 2. The reaction product was separated into three layers; an aqueous phase, an organic phase, and a portion soluble in neither of these phases. After the insoluble portion was filtered and separated, the aqueous and organic phases were separated by means of a separating funnel or centrifuge, and their respective solvents were evaporated under reduced pressure. The water-soluble portion was dissolved in methanol, the resultant solution was added to a fully stirred non-solvent for precipitation, and thus there was obtained colorless powder. Table 2 shows the measurement results of yield, softening point, and intrinsic viscosity.

From the infrared absorption spectra, nuclear magnetic resonance spectra, and titrated value of the base equivalent, the water-soluble polymers thus obtained were found to be carboxylate polyureas with a composition given by $y=0$ and $70 < 100x/(x+z) < 90$ as shown in Table 2. The water-insoluble portion in Examples 6 to 11 had a composition given by $y=0$ and $z \gg x$.

The same flocculation test performed for the polymer of Example 3 was made for the water-soluble polymers of Examples 6 to 8, and the greatest effect was attained with 9.0 ppm addition in all cases, completing the sedimentation within 2 minutes.

0.1 wt% aqueous solutions of the water-soluble polymers of Examples 9 and 10 were subjected to the same test performed for the polymer of Example 3, and the greatest effects were attained with 3.0 ppm addition, the sedimentation times being 4 and 3 minutes for Examples 9 and 10, respectively.

When an aqueous solution of the water-soluble polymer of Example 11 was added to an aqueous solution of transition metal salt, it caused precipitation, exhibiting the chelating ability.

The water-insoluble polymers of Examples 9 to 11 showed effective flocculation of an organometallic compound such as stannous octoate.

sponding to the index calculated from the measured value of the basic equivalent of CEXD and shown in Table 3 was dissolved in methylene chloride, and the resultant solution was gradually dropped into the stirred solution through the dropping funnel. After completion of such dropping, the solution was stirred for reaction at such temperature for such time as shown in Table 3. The reaction product was separated into three layers; an aqueous phase, an organic phase, and a portion soluble in neither of these phases, or was in an emulsion state. When in the former state, the product Table 2-(1)
Conditions & Results of Synthesis of Carboxylate Polyurea

| Example | CEHD g (mol) | Diisocyanate: g (mol) | Sodium hydroxide: g (mol) | Index | Solvent (ml) Water | Solvent (ml) Methylene chloride | Reaction Temperature & Time (° C/min) Dropping agitation | Reaction Temperature & Time (° C/min) Agitation | |
|---|---|---|---|---|---|---|---|---|---|
| 6 | 7.00 (0.037) | HMDI 5.76 (0.034) | 1.28 (0.032) | 1.0 | 100 | 50 | 20/60 | 20/65 | 40/60 |
| 7 | 5.00 (0.027) | HMDI 6.59 (0.039) | 0.91 (0.023) | 1.4 | 50 | 40 | 20/15 | 20/128 | 40/45 |
| 8 | | | | 1.6 | 50 | 40 | 20/11 | 20/157 | 40/40 |
| 9 | 4.00 (0.021) | MDI 6.28 (0.025) | 0.73 (0.018) | 1.0 | 70 | 50 | 20/15 | 20/30 | 40/30 |
| 10 | | MDI 6.86 (0.027) | | 1.4 | 70 | 50 | 20/25 | 20/250 | 40/30 |
| 11 | 5.00 (0.027) | 2,4-TDI 5.97 (0.034) | 0.91 (0.023) | 1.4 | 70 | 50 | 20/20 | 20/280 | 40/30 |

Table 2-(2)

| Example | Yield (%) Water-soluble portion | Yield (%) Water-insoluble portion | Softening point (° C) Water-soluble portion | Softening point (° C) Water-insoluble portion | Intrinsic viscosity (30° C, m-cresol) water-soluble portion | Precipitation solvent | Remarks |
|---|---|---|---|---|---|---|---|
| 6 | 50.5 | 39.0 | 120–130 | 225–263 | 0.195 | | x=0.773 (Water-soluble portion) Insoluble portion ηinh=0.560 |
| 7 | 73.9 | 16.0 | 135–140 | 244–258 | 0.202 | Precipitation by addition of methanol solution of the polymer to acetone | x=0.735 (Water-soluble portion) Insoluble portion ηinh=0.462 |
| 8 | 69.1 | 29.1 | 149–151 | 200–217 | 0.219 | | x=0.784 (Water-soluble portion) Insoluble portion ηinh=0.350 |
| 9 | 77.0 | 24.4 | 181–187 | 125–238 | 0.139 | | x=0.737 (Water-soluble portion) |
| 10 | 42.1 | 44.1 | 210–215 | 206–215 | 0.171 | Precipitation by addition of methanol solution of the polymer to acetonitrile | x=0.862 (Water-soluble portion) |
| 11 | 67.4 | 26.1 | 212–218 | 225–227 | 0.175 | | x=0.888 (Water-soluble portion) |

EXAMPLES 12 to 17

Employing the same apparatus as that of Example 1, a quantity of N-(2-carboxyethyl)-p-xylylenediamine (m.p.: 178.0 to 180.5° C., hereinafter referred to as CEXD) as shown in Table 3 and a solution of a quantity of sodium hydroxide corresponding to the equivalent calculated from the measured value of the acid equivalent of CEXD in a quantity of degassed distilled water as shown in Table 3 were placed in the flask, purged with nitrogen, and stirred while keeping the flask at 20° C. in the water bath. A quantity of diisocyanate correwas separated in the same manner as in Examples 1 to 11. On the other hand, when in the latter state, the emulsion was destroyed by means of the centrifuge, separated into three layers or reprecipitated directly into the non-solvent, and then separated into water-soluble and water-insoluble portions. Table 3 shows the measured results of yield, softening point, and intrinsic viscosity of colorless powder obtained by precipitation and of insoluble portion.

From the infrared absorption spectra, nuclear magnetic resonance spectra, and titrated value of the base equivalent, the thus obtained water-soluble polymers were found to be carboxylate polyureas with a composition given by $y=0$ and $65<100x/(x+z)<97$ as shown in Table 3. The water-insoluble portion in Examples 12 to 17 had a composition given by $y=0$ and $z>>x$.

The same flocculation test as made for the polymer of Example 3 was performed for the water-soluble polymers of Examples 12 to 14, and they all exhibited a good flocculating ability, while the greatest effect was given by the water-soluble polymer of Example 15. The time required to attain the equilibrium of sedimentation rate was 2.5 minutes with 3 ppm addition. Further, of 250ml of the suspension 215ml became clear 30 minutes after the whole suspension had been allowed to stand, whereas only 15ml became clear 30 minutes after the whole suspension had been allowed to stand when the water-soluble polymer was not added.

A film of 55μm thickness was prepared from the water-soluble polymer of Example 14 in the same manner as in Example 3. When measured under the same conditions as those of Example 3, the volume inherent resistivity of the film was $1.6\times10^{13}\Omega\cdot cm$ at 100V and $6.8\times10^{12}\Omega\cdot cm$ at 250V, and the surface inherent resistivity was $1.6\times10^{13}\Omega$ at 100V, $6.3\times10^{12}\Omega$ at 250V, and $4.3\times10^{12}\Omega$ at 500V, which are $10^3$ to $10^4$ lower than the electric resistances of conventional polymers.

A film of 62μm thickness was prepared from the water-soluble polymer of Example 16 in the same manner as in Example 3. When measured under the same conditions as those of Example 3, the volume inherent resistivity of the film was $4.4\times10^{11}\Omega\cdot cm$ at 100 V, $6.1\times10^{11}$ Ω·cm at 250V, and $1.5\times10^{11}\Omega\cdot cm$ at 500V, and the surface inhereit resistivity was $2.6\times10^{11}\Omega$ at 100V, $3.7\times10^{11}\Omega$ at 250V, and $9.5\times10^{11}\Omega$ at 500V.

When aqueous solutions of the water-soluble polymers of Examples 15 and 17 were added to an aqueous solution of transition metal salt, they caused precipitation, exhibiting the chelating ability.

Table 3

Conditions & Results of Synthesis of Carboxylate Polyurea (1)

| Example | CEXD g (mol) | Diisocyanate: g (mol) | Sodium hydroxide: g (mol) | Index | Solvent (ml) Water | Solvent (ml) Methylene chloride | Reaction Temperature & Time (° C/min) Dropping agitation | Reaction Temperature & Time (° C/min) Agitation | Reaction Temperature & Time (° C/min) |
|---|---|---|---|---|---|---|---|---|---|
| 12 | 6.00 (0.029) | HMDI 4.62 (0.028) | 1.23 (0.031) | 1.0 | 100 | 50 | 20/60 | 20/30 | 40/30 |
| 13 | | HMDI | | 1.2 | 40 | 40 | 20/15 | 20/120 | 40/30 |
| 14 | | HMDI 5.39 (0.032) | | 1.4 | 30 | 30 | 20/8 | 20/130 | 40/30 |
| 15 | 5.00 (0.024) | MDI 5.88 (0.023) | 1.02 (0.025) | 1.0 | 50 | 50 | 20/32 | 20/30 | 40/30 |
| 16 | | MDI 6.88 (0.028) | | 1.2 | 50 | 50 | 20/25 | 20/300 | 40/40 |
| 17 | | 2,4-TDI 5.59 (0.032) | | 1.4 | 50 | 50 | 20/20 | 20/230 | 40/50 |

(2)

| Example | Yield (%) Water-soluble portion | Yield (%) Water-insoluble portion | Softening point (° C) Water-soluble portion | Softening point (° C) Water-insoluble portion | Intrinsic viscosity (30° C, m-cresol) water-soluble portion | Precipitation solvent | Remarks |
|---|---|---|---|---|---|---|---|
| 12 | 58.0 | 7.6 | 131–134 | 233–238 | 0.153 | Precipitation by addition of methanol solution of the polymer to acetonitrile | x=0.809 (Water-soluble portion) |
| 13 | 79.4 | 7.4 | 148–152 | 170–180 | 0.314 | Precipitation by addition of methanol solution of the polymer to acetone | x=0.841 (Water-soluble portion) |
| 14 | 73.0 | 7.3 | 163–168 | 167–205 | 0.450 | | x=0.888 (Water-soluble portion) |
| 15 | 30.5 | 20.2 | 230–234 | 235–240 | 0.191 | | x=0.913 (Water-soluble portion) |
| 16 | 62.7 | 34.5 | 245–250 | 235–240 | 0.204 | precipitation by addition of methanol solution of the polymer to acetonitrile | x=0.962 (Water-soluble portion) |
| 17 | 65.0 | 20.5 | 182–188 | 215–228 | 0.136 | | x=0.664 (Water-soluble portion) |

EXAMPLE 18

Employing the same apparatus as that of Example 1, 8.00g (0.0395 mol) of N-(2-methyl-2-carboxyethyl) hexamethylenediamine (m.p.: 147.0 to 148.6° C.) and a solution of 1.58g (0.0396 mol) of sodium hydroxide in 50ml of degassed distilled water were placed in the flask, purged with nitrogen, and stirred while keeping the flask at 30° C. in a water bath. A solution of 6.65g (0.0396 mol) of hexane-1,6-diisocyanate in 50ml of carbon tetrachloride was dropped into the stirred solution through the dropping funnel for 38 minutes. Immediately after completion of such dropping, 0.1 wt% (as compared with the total weight of the content) of stannous octoate was added to the solution, which was further stirred for reaction at 30° C. for 142 minutes and then at 40° C. for 120 minutes. After completion of the reaction, the product, which was in an emulsion state, was separated into an aqueous phase, organic phase, and insoluble portion by means of the centrifuge. A solution of the water-soluble portion was added to fully stirred non-solvent acetone for precipitation, and thus there was obtained a substantially colorless, threadlike polymer.

From the infrared absorption spectra, nuclear magnetic resonance spectra, and titrated value of the base equivalent, the thus obtained water-soluble polymer was found to be a carboxylate polyurea with a composition given by y=0 and x=0.605. The water-insoluble portion had a composition given by y=0 and z>>x.

The measured values of yield, softening point, and intrinsic viscosity of the water-soluble polymer were 69.4%, 143.0 to 148.0° C., and 0.417 ($\eta_{inh}^{30° C.}$/m-cresol), respectively. A film of 0.11mm thickness was prepared from this polymer in the same manner as in Example 3. When measured under the same conditions as those of Example 3, the volume inherent resistivity of the film was $2.0\times10^{13}\Omega\cdot cm$ at 100V, $5\times10^{12}\Omega\cdot cm$ at 250V, $4.7\times10^{12}\Omega\cdot cm$ at 500V, and $1.6\times10^{12}\Omega\cdot cm$ at 1,000V, and the surface inherent resistivity was 6.0 to $8.3\times10^{12}\Omega$ at 100V, 250V, 500V and 1,000V.

The charge amount measured under the same conditions as those of Example 3 was 3.5 e.s.u./cm$^2$.

EXAMPLE 19

Employing the same apparatus as that of Example 1, 8.00g (0.0395 mol) of N-(2-methyl-2-carboxyethyl) hexamethylenediamine and a solution of 1.58g (0.0396 mol) of sodium hydroxide in 50ml of degassed distilled water were placed in the flask, purged with nitrogen, and stirred while keeping the flask at 30° C. in a water bath. A solution of 9.89g (0.0396 mol) of diphenylmethane-4,4'-diisocyanate in 50ml of carbon tetrachloride was dropped into the stirred solution through the dropping funnel over 34 minutes. Immediately after completion of such dropping, 0.1 wt% (as compared with the total weight of the content) of stannous octoate was added to the solution. The resultant solution was further stirred for reaction at 30° C. for 146 minutes and then at 40° C. for 136 minutes after addition of 40ml of distilled water to improve the efficiency of agitation which had been deteriorated due to the absorption of the solvent by the product after addition of the catalyst. After completion of the reaction, the product was separated into water-soluble and water-insoluble portions by means of the centrifuge. A solution of the water-soluble portion was added to fully stirred acetonitrile for precipitation, and thus there was obtained a substantially colorless, threadlike polymer.

From the infrared absorption spectra, nuclear magnetic resonance spectra, and titrated value of the base equivalent, the thus obtained water-soluble polymer was found to be a carboxylate polyurea with a composition given by y=0 and x=0.744. The water-insoluble portion had a composition given by y=0 and z>>x.

The measured values of yield, softening point, and intrinsic viscosity of the water-soluble polymer were 60.6%, 220.0 to 225.0° C., and 0.191 ($\eta_{inh}^{30° C.}$/m-cresol), respectively. A film of 0.344mm thickness was prepared from this polymer in the same manner as in Example 3. When measured under the same conditions as those of Example 3, the volume inherent resistivity of the film was $1.6\times10^{12}\Omega\cdot cm$ at 100V, $8.7\times10^{11}\Omega\cdot cm$ at 250V, $4.5\times10^{11}\Omega\cdot cm$ at 500V, and $8.6\times10^{10}\Omega\cdot cm$ at 1,000V, and the surface inherent resistivity was 4.2 to $2.6\times10^{12}\Omega$ at voltages ranging from 100V to 1,000V — sufficiently low electric resistance free from any dielectric breakdown.

The charge amount measured in the same manner as in Example 3 was 1.64 e.s.u./cm$^2$.

EXAMPLE 20

Employing the same apparatus as that of Example 1, 10.0g (0.0555 mol) of N-(2-carboxyethyl)-p-phenylenediamine (m.p.: 183.0 to 185.0° C.) and a solution of 2.21g (0.0553 mol) of sodium hydroxide in 50ml of degassed distilled water were placed in the flask, purged with nitrogen, and stirred while keeping the flask at 22° C. A solution of 9.29g (0.0553 mol) of hexane-1,6-diisocyanate in 50ml of carbon tetrachloride was dropped into the stirred solution through the dropping funnel over 25 minutes. Immediately after completion of such dropping, 0.1 wt% (as compared with the total weight) of stannous octoate was added to the solution, which was further stirred for reaction at 20° C. for 155 minutes and at 45° C. for 345 minutes. After completion of the reaction, the product, which was in an emulsion state, was added to fully stirred non-solvent acetonitrile for precipitation, and then separated into water-soluble and water-insoluble portions. The water-soluble portion was again added to acetonitrile for precipitation, and thus there was obtained a dark-grey polymer.

From the infrared absorption spectra, nuclear magnetic resonance spectra, and titrated value of the base equivalent, the thus obtained water-soluble polymer was found to be a carboxylate polyurea with a composition given by y=0 and x=0.907. The water-insoluble portion had a composition given by y=0 and z>>x.

The measured values of yield, softening point, and intrinsic viscosity of the water-soluble polymer were 75.9%, 228 to 230° C., and 0.305 ($\eta_{inh}^{30° C.}$/m-cresol), respectively.

This water-soluble polymer had the chelating ability with transition metals. A film of 0.40mm thickness was prepared from the polymer in the same manner as in Example 3. When measured under the same conditions as those of Example 3, the volume inherent resistivity of the film was $2.8\times10^{10}\Omega\cdot cm$ at 100V, $1.2\times10^{9}\Omega\cdot cm$ at 250V, $9.3\times10^{7}\Omega\cdot cm$ at 500V, and the surface inherent resistivity was $3.0\times10^{10}\Omega$ at 100V, $5.1\times10^{9}\Omega$ at 250V, and $5.6\times10^{9}\Omega$ at 500V — sufficiently low electric resistances.

The charge amount measured in the same manner as in Example 3 was 0.44 e.s.u./cm$^2$ — a very low level.

The dielectric properties of the water-soluble polymer (of Example 20) were measured. The measurement was conducted at 20° C. by pressure-molding the powdered polymer under a pressure of 100 kg/cm$^2$. Consequently, there was exhibited such low dielectric constants as shown below, despite the polar radical contained.

| Hz | $\epsilon'$ | tan $\delta$ | $\epsilon''$ |
|---|---|---|---|
| 60 | 3.76 | 0.231 | 0.870 |
| 1,000 | 2.94 | 0.108 | 0.317 |
| 10,000 | 2.64 | 0.0697 | 0.184 |

EXAMPLE 21

Employing the same apparatus as that of Example 1, 8.00g (0.0194 mol) of N,N'-di-(2-carboxyethyl)-3,3'-dichloro-4,4'-diaminodiphenylmethane (m.p.: 163.0 to 165.0° C.) and a solution of 1.56g (0.039 mol) of sodium hydroxide in 50ml of degassed distilled water were placed in the flask, purged with nitrogen, and stirred while keeping the flask at 25° C. in the water bath. A solution of 4.86g (0.0194 mol) of diphenylmethane-4,4'-diisocyanate in 50ml of carbon tetrachloride was dropped into the stirred solution through the dropping funnel for 40 minutes. Thirty minutes after completion of such dropping, 0.1 wt% (as compared with the total weight) of stannous octoate was added to the solution, which was further stirred for reaction at 40° C. for continuous 920 minutes. The product was separated into an aqueous phase, organic phase, and insoluble portion. After the insoluble portion was filtered and separated, the aqueous and organic phases were separated from each other by means of the separating funnel. The aqueous phase was added to fully stirred nonsolvent acetonitrile for precipitation, and thus there was obtained a powdered polymer.

From the infrared absorption spectra, nuclear magnetic resonance spectra, and titrated value of the base equivalent, the thus obtained water-soluble polymer was found to a carboxylate polyurea with a composition given by $y=0$ and $x=0.831$. The water-insoluble portion had a composition given by $y=0$ and $z>>x$.

The measured values of yield, softening point, and intrinsic viscosity of the water-soluble polymer were 90.8%, 195 to 200° C., and 0.103 ($\eta_{inh}^{30° C.}$/m-cresol), respectively.

When an aqueous solution of this water-soluble polymer was added to an aqueous solution of transition metal salt, it caused precipitation, revealing that the polymer has a chelating ability.

EXAMPLE 22

Employing the same apparatus as that of Example 1, 3.00g (0.0159 mol) of N-(2-carboxyethyl) hexamethylenediamine (CEHD) and 0.329g (0.0137 mol) of lithium hydroxide - this corresponds to the equivalent calculated from the measured value of the acid equivalent of CEHD - as well as 40ml of dimethylsulfoxide were placed in the flask, stirred for dissolution, purged with nitrogen, and kept at 18° C. in a water bath. 10.9g of ω,ω'-diisocyanate polypropylene glycol (NCO%=11.3%) corresponding to the equivalent calculated from the measured value of the base equivalent of CEHD was dissolved in 10ml of dimethylsulfoxide, and the resultant solution was dropped into the aforesaid solution through the dropping funnel over 35 minutes. After completion of such dropping, 0.1 wt% (as compared with the total weight) of stannous octoate was added to the solution, which was further stirred for reaction at 18° C. for 145 minutes and then at 80° C. for 120 minutes. An insoluble portion produced in the dimethylsulfoxide was filtered and separated, and the resultant filtrate was added to fully stirred non-solvent acetone for precipitation, and thus there was obtained a slightly yellowish, powdered polymer.

From the infrared absorption spectra, nuclear magnetic resonance spectra, and titrated value of the basic equivalent, the above polymer was found to be a carboxylate polyurea with a composition given by $y=0$, $z=0$ and $x=1$. The water-insoluble portion has a composition given by $y=0$ and $z>>x$.

The measured values of its yield, softening point, and intrinsic viscosity of the water-soluble polymer were 60.0%, 117 to 143° C., and 0.188 ($\eta_{inh}^{30° C.}$/m-cresol), respectively.

When an aqueous solution of this water-soluble polymer was added to an aqueous solution of transition metal salt, it produced precipitation, exhibiting the chelate effect.

EXAMPLE 23

19.4g. of N-(2-carboxyethyl) hexamethylenediamine lithium salt, 400g of ω,ω'-di-(aminotricarbamyl) polytetramethylene glycol (amine value 28.1), 19.8g of 4,4'-diaminodiphenylmethane, 11.6g of hexamethylenediamine, and 600g of alumina powder were placed in a 2l beaker, heated to 90 to 100° C. in an oil bath for fusion-mixing, and then cooled down to 60° C. 69.7g of 1-methylbenzenediisocyanate (1-methylbenzene-2,4-diisocyanate/1-methylbenzene-2,6-diisocyanate ratio 80:20) was added to the cooled mixture, and again fully stirred and mixed. The resultant mixture was cast between Teflon-coated parallel iron plates, and left at room temperature for 2 hours, then at 80° C. for 2 hours, and finally at 120° C. for additional 2 hours. Thereafter, the mixture was cooled down to the room temperature and removed from the mold, and thus there was prepared a plate 1.0mm thick.

When measured under the same conditions as those of Example 3, the electric charge amount of this plate was as low as 3 to 4 e.s.u./cm². Thus, this molded product exhibited a satisfactory antistatic property.

The thus obtained polymer was found to be a carboxylate polyurea with a composition given by $x=0.25$ and $y=0.75$.

EXAMPLE 24

32.1g of N-(2-carboxyethyl)-p-xylylenediamine lithium salt, 400g of ω,ω'-di-(aminotricarbamyl) polytetramethylene glycol (amine value 28.1), 6.8g of p-xylylenediamine, 1.20g of water (as a blowing agent and component z), and 37.5g of barium sulfate powder were placed in a 2l beaker, heated to 110 to 120° C. in the oil bath to give homogeneous melted mixture, and then the mixture was cooled down to 55° C. 6.00g of silicone oil as a foam stabilizer, 0.30g of stannous octoate, and 1.50g of triethylenediamine were added to the cooled mixture, and stirred and mixed. 61.6g of hexane-1,6-diisocyanate was further added to the mixture, and fully stirred and mixed. The resultant mixture was injected into a 2l paper cup, polymerized at the room temperature for 2 hours and then at 100° C. for 3 hours, and thus there was obtained a molding. As a result of the measurement of the carboxylate equivalent by titration as well as of the nitrogen content by elemental analysis, this molding was found to be a carboxylate polyurea with a composition given by $x=0.481$, $y=0.493$ and $z=0.026$.

A cube with dimensions 5.0×5.0×5.0cm was cut out from the molding, and its electric charge amount was measured under the same conditions as those of Example 3, provided the cube was subjected to an applied voltage of 10KV. While the charge amount immediately after the charging had been 1.8 e.s.u./cm², it was attenuated to approximately 1/15 to 1/20 of the initial value when measured after the cube was left in the same atmosphere and subjected to natural discharge for 15 minutes, exhibiting a satisfactory antistatic property.

EXAMPLE 25

4.00g (0.0206 mol) of N-(2-carboxyethyl) hexamethylenediamine lithium salt, 2.5g of lithium chloride as an electrolyte solubilizing agent, and 110ml of dimethylsulfoxide (DMSO) were placed together in the same flask as that of Example 1, purged with nitrogen, and stirred at 70° C. for dissolution. Thereafter, with the flask kept at 20° C., a solution of 3.46g (0.0206 mol) of hexamethylenediisocyanate in 20ml of DMSO was dropped into the stirred solution through the dropping funnel over 15 minutes. After completion of such dropping, 0.28g of dibutyl tin dilaurate was added to the solution, which was further stirred for reaction at 22° C. for 120 minutes and then at 70° C. for 170 minutes. The product, most of which was insoluble in DMSO, was filtered and separated. This insoluble portion was dissolved in water, and the resultant solution was further separated into water-soluble and water-insoluble portions. The filtrate was added to acetonitrile for precipitation, and thus there was obtained a pale yellow, powdered polymer.

The measured values of yield and intrinsic viscosity of this water-soluble polymer were 58.3% and 0.158 ($\eta_{inh}^{30°\ C.}$/m-cresol), respectively, the polymer exhibiting a very high moisture-absorptive property. From the nuclear magnetic resonance spectra, this polymer was found to be a carboxylate polyurea composed of x-unit alone.

EXAMPLE 26

Employing the same apparatus as that of Example 1, 4.93g (0.0265 mol) of N-(2-carboxyethyl)-p-phenylenediamine lithium salt, 2.0g of lithium chloride as an electrolyte solubilizing agent, and 80ml of dimethylsulfoxide (DMSO) were placed together in the flask, purged with nitrogen, and stirred at 40° C. for dissolution. Thereafter, with the flask kept at 22° C., a solution of 6.62g (0.0265 mol) of 4,4'-diphenylmethanediisocyanate in 20ml of DMSO was dropped into the stirred solution through the dropping funnel over 13 minutes. After completion of such dropping, 0.22g of dibutyl tin dilaurate was added to the solution, which was further stirred for reaction at 20° C. for 110 minutes and then at 71° C. for 125 minutes. An insoluble portion of the product was filtered and separated, and the resultant filtrate was added to acetonitrile for precipitation, and thus there was obtained a black, powdered polymer.

The measured values of yield, softening point, and intrinsic viscosity of this polymer were 80.1%, 230 to 237° C., and 0.152 ($\eta_{inh}^{30°\ C.}$/DMSO), respectively. From the nuclear magnetic resonance spectra, this polymer was found to be a carboxylate polyurea composed of x-unit alone.

EXAMPLE 27

Employing the same apparatus as that of Example 1, 4.00g (0.0206 mol) of N-(2-carboxyethyl) hexamethylenediamine lithium salt, 2.5g of lithium chloride as an electrolyte solubilizing agent, and 110ml of dimethylsulfoxide (DMSO) were placed together in the flask, purged with nitrogen, and stirred at 70° C. for dissolution. Thereafter, with the flask dept at 25° C., a solution of 5.15g (0.0206 mol) of 4,4'-diphenylmethanediisocyanate in 20ml of DMSO was dropped into the stirred solution through the dropping funnel over 35 minutes. After completion of such dropping, 0.28 g of dibutyl tin dilaurate was added to the solution, which was further stirred for reaction at 26° C. for 110 minutes and then at 71° C. for 120 minutes. An insoluble portion of the product was filtered, and the resultant filtrate was added to acetonitrile for precipitation, and thus there was obtained a substantially colorless, powdered polymer.

The measured values of yield, softening point, and intrinsic viscosity of this water-soluble polymer were 62.9%, 207 to 218° C., and 0.229 ($\eta_{inh}^{30°\ C.}$/DMSO), respectively. From the nuclear magnetic resonance spectra, this polymer was found to be a carboxylate polyurea composed of x-unit alone.

EXAMPLE 28

Employing the same apparatus as that of Example 1, 4.00g (0.0206 mol) of N-(2-carboxyethyl) hexamethylenediamine lithium salt, 1.24g (0.0207 mol) of ethylenediamine, 2.0g of lithium chloride as an electrolyte solubilizing agent, and 100ml of dimethylsulfoxide (DMSO) were placed together in the flask, purged with nitrogen, and stirred at 70° C. for dissolution. Thereafter, with the flask kept at 30° C., a solution of 10.32g (0.0413 mol) of 4,4'-diphenylmethanediisocyanate in 20ml of DMSO was dropped into the stirred solution through the dropping funnel for 17 minutes. After completion of such dropping, 0.27g of dibutyl tin dilaurate was added to the solution, which was further stirred for reaction at 30° C. for 200 minutes and then at 70° C. for 120 minutes. The product, which was a colorless, transparent, highly viscous liquid, was added to acetonitrile for precipitation, and thus there was obtained a colorless, fibrous polymer.

The measurement values of yield, softening point, and intrinsic viscosity of this polymer were 100%, 210 to 223° C., and 0.364 ($\eta_{inh}^{30°\ C.}$/DMSO), respectively. From the nuclear magnetic resonance spectra, this polymer was found to be a carboxylate polyurea composed of x- and y-units.

What we claim is:

1. A urea compound having carboxylate radical, represented by the formula:

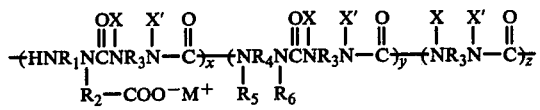

where $R_1$ is a divalent hydrocarbon-based radical having 2 to 17 carbon atoms or a divalent polymer radical having an average molecular weight of 10,000 or less; $R_2$ is

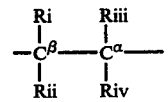

radical with the α-carbon directly bonded with the carbon atom of the carboxylate radical; Ri, Rii, Riii and Riv are each independently hydrogen atom, a monovalent hydrocarbon-based radical having 1 to 10 carbon atoms or any other monovalent radical unreactive with isocyanato or amino radicals, at least one of Ri and Rii being hydrogen atoms; $R_3$ is a divalent hydrocarbon-based radical having 4 to 25 carbon atoms, or a polyether or polyester radical having an average molecular weight of 10,000 or less; $R_4$ is a divalent hydrocarbon-based radical having 2 to 17 carbon atoms; $R_5$ and $R_6$ are each independently hydrogen atom or a monovalent hydrocarbon-based radical having 1 to 8 carbon atoms, or $R_5$ and $R_6$ are divalent hydrocarbon-based radicals forming together by mutual bond a carbon chain having 2 to 13 carbon atoms or its side chain substituent; X and X' are each independently hydrogen atom or —CONH— radical; $M^+$ is a cation; and x, y and z are values indicating the relative molar proportions of the respective corresponding units and complying with required normalizations: $x+y+z=1$ and $0.1 > 100x/(x+y+z) \leq 100$.

2. A urea compound according to claim 1, wherein said y and z are each zero, and which is represented by the formula:

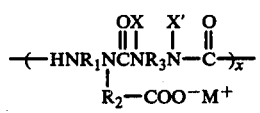

where $R_1$, $R_2$, $R_3$, X, X' and $M^+$ are as defined above.

3. A urea compound according to claim 1, wherein said z is zero, and which is represented by the formula:

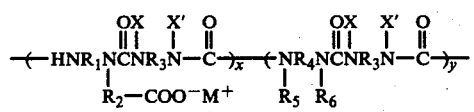

where $R_1$, $R_2$, $R_3$, $R_4$, $R_5$, $R_6$, X, X' and $M^+$ are as defined above, and x and y are values indicating the relative molar proportions of the respective corresponding units and complying with the required normalizations: $x+y=1$ and $0.1 \leq 100x/(x+y) < 100$.

4. A urea compound according to claim 1, wherein said y is zero, and which is represented by the formula:

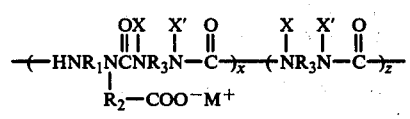

where $R_1$, $R_2$, $R_3$, X, X' and $M^+$ are as defined above, and x and z are values indicating the relative molar proportions of the respective corresponding units and complying with the required normalizations: $x+z=1$ and $0.1 \leq 100x/(x+z) < 100$.

5. A urea compound according to claim 1, wherein said x, y and z are each more than zero, and which is represented by the formula:

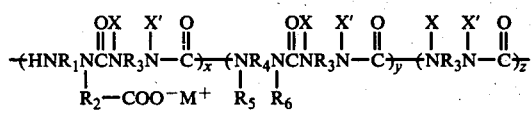

where $R_1$, $R_2$, $R_3$, $R_4$, $R_5$, $R_6$, X, X' and $M^+$ are as defined above, and x, y and z are values indicating the relative molar proportions of the respective corresponding units and complying with the required normalizations: $x+y+z=1$ and $0.1 \leq 100x/(x+y+z) < 100$.

6. A urea compound according to claim 1, wherein the molar ratio of the —CONH— radical occupies 30% or less over the total molar amounts of X and X' radicals.

7. A urea compound according to claim 1, wherein said $R_1$ is a radical selected from the group consisting of aliphatic hydrocarbon radicals having 2 to 17 carbon atoms; alicyclic or aliphatic-substituted alicyclic hydrocarbon radicals having 6 to 15 carbon atoms; aromatic, aliphatic-substituted aromatic and aliphatic-substituted alicyclic-substituted aromatic hydrocarbon radicals; derivatives thereof substituted with non-hydrocarbon radicals; and $\omega,\omega'$-polyether and $\omega,\omega'$-polyester radicals each having a repeating unit of 2 to 20 carbon atoms and an average molecular weight of 104 to 10,000.

8. A urea compound according to claim 7, wherein said $R_1$ is ethylene, hexamethylene, p-phenylene, p-xylylene, 4,4'-diphenylenemethane or 3,3'-dichloro-4,4'-diphenylenemethane radical.

9. A urea compound according to claim 1, wherein said Ri, Rii, Riii and Riv are radicals each selected from the group consisting of aliphatic, alicyclic and aromatic hydrocarbon radicals each having 1 to 10 carbon atoms; monovalent hydrocarbon radicals derived from the combination thereof; halogen atom; cyano radical; amide radical; imide radical; nitro radical; ester radical; alkoxyl radical; aryloxy radical; ketone radical; and oxycarbonyl radical.

10. A urea compound according to claim 9, wherein said $R_2$ is ethylene or α-methylethylene radical.

11. A urea compound according to claim 1, wherein said $R_3$ is a radical selected from the group consisting of aliphatic hydrocarbon radicals having 4 to 16 carbon atoms, alicyclic hydrocarbon radicals having 8 to 20 carbon atoms, aliphatic-substituted aromatic hydrocarbon radicals having 9 to 20 carbon atoms, alicyclic-substituted aromatic hydrocarbon radicals having 12 to 20 carbon atoms, aromatic hydrocarbon radicals having 8 to 25 carbon atoms, and $\omega,\omega'$-polyether and $\omega,\omega'$-polyester radicals each having an average molecular weight of 302 to 10,000.

12. A urea compound according to claim 11, wherein said $R_3$ is hexamethylene, diphenylmethane, 1-methyl-2,4-phenylene or 1-methyl-2,6-phenylene radical.

13. A urea compound according to claim 1, wherein said M is one member selected from alkali metals, alkaline earth metals and tertiary amines.

14. A method for producing a urea compound having carboxylate radical and represented by the formula:

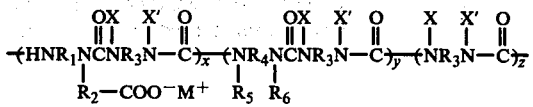

which method comprises reacting an aminoaminocarboxylic acid salt represented by the formula:

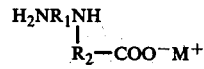

with a diisocyanate represented by the formula:

optionally in the presence of water and/or a diamine represented by the formula:

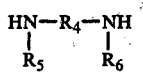

where $R_1$ is a divalent hydrocarbon-based radical having 2 to 17 carbon atoms or a divalent polymer radical having an average molecular weight of 10,000 or less; $R_2$ is

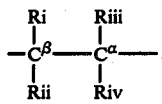

radical with the α-carbon directly bonded with the carbon atom of the carboxylate radical, Ri, Rii, Riii and Riv are each independently hydrogen atom, a monovalent hydrocarbon-based radical having 1 to 10 carbon atoms or any other monovalent radical unreactive with isocyanato or amino radicals, at least one of Ri and Rii being hydrogen atom; $R_3$ is a divalent hydrocarbon-based radical having 4 to 25 carbon atoms, or a polyether or polyester radical having an average molecular weight of 10,000 or less; $R_4$ is a divalent hydrocarbon-based radical having 2 to 17 carbon atoms; $R_5$ and $R_6$ are each independently hydrogen atom or a monovalent hydrocarbon-based radical having 1 to 8 carbon atoms, or $R_5$ and $R_6$ are divalent hydrocarbon-based radicals forming together by mutual bond a carbon chain having 2 to 13 carbon atoms or its side chain substituent, X and X' are hydrogen atom or —CONH— radical; M+ is a cation; and x, y and z are values indicating the relative molar proportions of the respective corresponding units and complying with the required normalizations: $x+y+z=1$ and $0.1 \leq 100x/(x+y+z) \leq 100$.

15. A method according to claim 14, wherein only the aminoaminocarboxylic acid salt and the diisocyanate are the indispensable reactants, and which produces a urea compound represented by the formula:

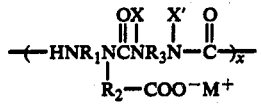

where $R_1$, $R_2$, $R_3$, X, X' and M+ are as defined above.

16. A method according to claim 14, wherein the aminoaminocarboxylic acid salt, the diisocyanate and the diamine are the indispensable reactants, and which produces a urea compound represented by the formula:

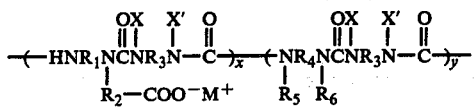

where $R_1$, $R_2$, $R_3$, $R_4$, $R_5$, $R_6$, X, X' and M+ are as defined above, and x and y are values indicating the relative molar proportions of the respective corresponding units and complying with the required normalizations: $x+y=1$ and $0.1 \leq 100x/(x+y) < 100$.

17. A method according to claim 14, wherein the aminoaminocarboxylic acid salt, the diisocyanate and the water are indispensable reactants, and which produces a urea compound represented by the formula:

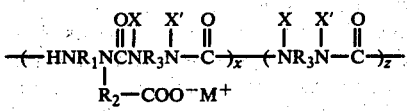

where $R_1$, $R_2$, $R_3$, X, X' and M+ are as defined above, and x and z are values indicating the relative molar proportions of the respective corresponding units and complying with the required normalizations: $x+z=1$ and $0.1 \leq 100x/(x+z) < 100$.

18. A method according to claim 14, wherein all the aminoaminocarboxylic acid salt, the diisocyanate, the diamine and the water are indispensable reactants, and which produces a urea compound represented by the formula:

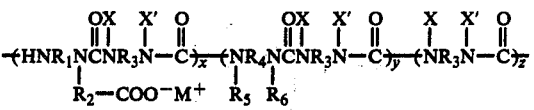

where $R_1$, $R_2$, $R_3$, $R_4$, $R_5$, $R_6$, X, X' and M+ are as defined above, and x, y and z are values indicating the relative molar proportions of the respective corresponding units and complying with the required normalizations: $x+y+z=1$ and $0.1 \leq 100x/(x+y+z) < 100$.

19. A method according to claim 14, wherein said reaction is an interfacial polyaddition reaction.

20. A method according to claim 19, wherein water is used as a solvent for the aminoaminocarboxylic acid salt, and a water-insoluble organic solvent which does not react with the aminoaminocarboxylic acid salt and the diisocyanate is used as a solvent for the diisocyanate.

21. A method according to claim 20, wherein said organic solvent is carbon tetrachloride or methylene chloride.

22. A method according to claim 19, wherein said aminoaminocarboxylic acid salt is prepared by the addition of the base M to the corresponding aminoaminocarboxylic acid before the reaction.

23. A method according to claim 19, wherein the reaction is performed through a first step wherein the reaction is carried out at a relatively low temperature and in the absence of a catalyst, a second step wherein the reaction is carried out in the presence of a catalyst, a third step wherein the reaction is carried out at a relatively high temperature, or a combination thereof.

24. A method according to claim 20, wherein the concentration of each of the reactants in each of the solvents is 0.1% to 40% by weight.

25. A method according to claim 20, wherein the concentration of each of the reactants in each of the solvents is 1% to 30% by weight.

26. A method according to claim 20, wherein the reaction is carried out at a temperature of more than a freezing point of the reaction system up to less than 100° C.

27. A method according to claim 26, wherein the reaction is carried out at a temperature of less than a boiling point of the organic solvent.

28. A method according to claim 20, wherein the reaction is carried out at a temperature of 0° C. to 60° C.

29. A method according to claim 20, wherein the reaction is carried out at a temperature of 0° C. to 35° C.

30. A method according to claim 23, wherein the reaction is carried out by effecting the first step to complete most of the reaction and subsequently conducting the third step at a temperature 5° C. to 35° C. higher than the temperature at which the first step is effected to finally complete the reaction.

31. A method according to claim 14, wherein the reaction is a solution polymerization.

32. A method according to claim 31, wherein a polar aprotic solvent is used.

33. A method according to claim 32, wherein an electrolyte which does not react with the diisocyanate, the aminoaminocarboxylic acid salt and the polar aprotic solvent is added as a solubilizing agent.

34. A method according to claim 32, wherein the corresponding aminoaminocarboxylic acid and the base M are added to the polar aprotic solvent to neutralize, thereby forming a solution of the aminoaminocarboxylic acid salt.

35. A method according to claim 34, wherein a neutral dehydrating agent is added so as to remove water produced during the neutralization.

36. A method according to claim 32, wherein a solution of the diisocyanate is slowly added to a solution of the aminoaminocarboxylic acid salt.

37. A method according to claim 32, wherein the reaction is conducted under an inert atmosphere.

38. A method according to claim 31, wherein the reaction is conducted at a temperature of more than a freezing point of the reaction system up to 200° C.

39. A method according to claim 31, wherein the reaction is conducted at a temperature of more than a freezing point of the reaction system up to 100° C.

40. A method according to claim 31, wherein the reaction is conducted through a first step wherein the reaction is carried out at a relatively low temperature and in the absence of a catalyst, a second step wherein the reaction is carried out in the presence of a catalyst, a third step wherein the reaction is carried out at a relatively high temperature, or a combination thereof.

41. A method according to claim 40, wherein the reaction is carried out by effecting the first step to complete most of the reaction and subsequently conducting the third step at a temperature 5° C. to 100° C. higher than the temperature at which the first step is effected to finally complete the reaction.

42. A method according to claim 31, wherein the concentration of each of the reactants in each of the solvents is 1% to 50% by weight.

43. A method according to claim 31, wherein the concentration of each of the reactants in each of the solvents is 5% to 30% by weight.

44. A method according to claim 14, wherein the reaction is a solvent-free polymerization.

45. A method according to claim 40, wherein the reactants are mixed, charged in a container or a casting mold and reacted there.

46. A method according to claim 44, wherein the reaction is carried out through a first step wherein the reaction is conducted at a relatively low temperature and in the absence of a catalyst, a second step wherein the reaction is conducted in the presence of a catalyst, or a combination thereof.

47. A method according to claim 46, wherein the first step is effected at a temperature of 0° C. to 100° C.

48. A method according to claim 46, wherein the reaction is carried out through the combination of said first and second steps, and the second step is effected at a temperature of 50° C. to 200° C.

49. A method according to claim 44, wherein a diluent filler is added.

50. A method according to claim 49, wherein the diluent filler is alumina powder or barium sulfate powder.

* * * * *